(12) United States Patent
Wang

(10) Patent No.: US 11,020,086 B2
(45) Date of Patent: Jun. 1, 2021

(54) BREAST ULTRASOUND SCANNING

(71) Applicant: Shih-Ping Wang, Palo Alto, CA (US)

(72) Inventor: Shih-Ping Wang, Palo Alto, CA (US)

(*) Notice: Subject to any disclaimer, the term of this patent is extended or adjusted under 35 U.S.C. 154(b) by 0 days.

(21) Appl. No.: 15/975,544

(22) Filed: May 9, 2018

(65) Prior Publication Data

US 2018/0256130 A1  Sep. 13, 2018

Related U.S. Application Data

(63) Continuation-in-part of application No. 15/244,950, filed on Aug. 23, 2016, now abandoned, which is a continuation of application No. 14/070,336, filed on Nov. 1, 2013, now Pat. No. 9,420,991, which is a continuation-in-part of application No. 13/296,023, filed on Nov. 14, 2011, now Pat. No. 8,579,819, which is a continuation of application No. 11/513,481, filed on Aug. 30, 2006, now abandoned, said application No. 15/244,950 is a continuation of application No. 14/076,989, filed on Nov. 11, 2013, now Pat. No. 9,498,184, said application No. 15/244,950 is a continuation of application No. 14/077,050, filed on Nov. 11, 2013, now abandoned.

(60) Provisional application No. 62/647,813, filed on Mar. 25, 2018, provisional application No. 62/503,869, filed on May 9, 2017, provisional application No. 60/713,282, filed on Sep. 1, 2005, provisional application No. 61/769,913, filed on Feb. 27, 2013.

(51) Int. Cl.
*A61B 8/08* (2006.01)
*A61B 8/00* (2006.01)
*A61B 8/14* (2006.01)

(52) U.S. Cl.
CPC ............ *A61B 8/0825* (2013.01); *A61B 8/14* (2013.01); *A61B 8/4209* (2013.01); *A61B 8/4218* (2013.01); *A61B 8/4455* (2013.01); *A61B 8/4461* (2013.01); *A61B 8/4494* (2013.01); *A61B 8/463* (2013.01); *A61B 8/483* (2013.01); *A61B 8/54* (2013.01); *A61B 8/145* (2013.01); *A61B 8/4281* (2013.01); *A61B 8/4405* (2013.01)

(58) Field of Classification Search
CPC ... A61B 8/0825; A61B 8/4209; A61B 8/4461; A61B 8/4218; A61B 8/483; A61B 8/54; A61B 8/145; A61B 8/4281; A61B 8/4405
See application file for complete search history.

(56) References Cited

U.S. PATENT DOCUMENTS

| | | | |
|---|---|---|---|
| 4,886,494 A * | 12/1989 | Morifuji | A61M 1/0023 604/74 |
| 5,526,394 A | 6/1996 | Siczek et al. | |
| 6,304,770 B1 * | 10/2001 | Lee | A61B 6/0414 600/427 |
| 8,579,819 B2 | 11/2013 | Wang et al. | |
| 9,420,991 B2 | 8/2016 | Wang | |
| 9,498,184 B2 | 11/2016 | Wang | |
| 2002/0188198 A1 | 12/2002 | Hong | |

(Continued)

OTHER PUBLICATIONS

Jun. 10, 2019 International Search Report and Written Opinion in connection with International Application No_ PCT/ US19/22715.

*Primary Examiner* — Hien N Nguyen
(74) *Attorney, Agent, or Firm* — Wissing Miller LLP

(57) ABSTRACT

A method and apparatus for acquisition of volumetric breast images for screening and/or diagnosing breast cancers using a rotary scanning template and transducer.

11 Claims, 15 Drawing Sheets

(56) References Cited

U.S. PATENT DOCUMENTS

| | | |
|---|---|---|
| 2004/0068797 A1 | 4/2004 | Smith et al. |
| 2004/0092826 A1* | 5/2004 | Corbeil ............... A61B 5/0091 |
| | | 600/476 |
| 2007/0014567 A1 | 1/2007 | Rossner et al. |
| 2007/0038085 A1* | 2/2007 | Zhang ................ A61B 6/463 |
| | | 600/437 |
| 2007/0055159 A1 | 3/2007 | Wang et al. |
| 2008/0194959 A1 | 8/2008 | Wang et al. |
| 2009/0080604 A1 | 3/2009 | Shores et al. |
| 2014/0323866 A1 | 10/2014 | Wang et al. |
| 2014/0378946 A1* | 12/2014 | Thompson ............ A61M 1/062 |
| | | 604/514 |
| 2015/0094589 A1* | 4/2015 | Chen ................... A61B 8/4218 |
| | | 600/445 |
| 2015/0126864 A1* | 5/2015 | Buelow ............... A61B 8/0825 |
| | | 600/437 |
| 2015/0265243 A1* | 9/2015 | Kelly ................... A61B 8/4444 |
| | | 600/443 |
| 2017/0095225 A1 | 4/2017 | Wang et al. |

\* cited by examiner

BREAST ULTRASOUND SCANNING

CROSS-REFERENCE TO RELATED APPLICATIONS

This application claims the benefit of U.S. Provisional Application 62/647,813 filed Mar. 25, 2018; and U.S. Provisional Application 62/503,869 filed May 9, 2017. This application is a continuation-in-part of U.S. application Ser. No. 15/244,950 filed on Aug. 23, 2016 (which is published as US 2014/0323866), which is a continuation of U.S. application Ser. No. 14/077,050 filed on Nov. 11, 2013 (which is published as US 2014/0323866). This application relates to International Application No. PCT/US13/69468 filed on Nov. 11, 2013 (which is published as WO 2014/133605); U.S. Pat. Nos. 8,579,819; 9,420,991; and 9,498,184. U.S. application Ser. No. 14/077,050 is a continuation of U.S. application Ser. No. 13/296,023 filed Nov. 14, 2011 (now issued as U.S. Pat. No. 8,579,819), which is a continuation of U.S. application Ser. No. 11/513,481 filed Aug. 30, 2006 and claimed the benefit of U.S. Provisional Application No. 60/713,282 filed on Sep. 1, 2005. The entire contents of all of the above patents and patent applications are hereby incorporated by reference herein. Also incorporated by reference herein are the contents of all of the patent applications and patents and other publications cited below. With respect to common subject matter that is expressly stated or is incorporated by reference herein, this application claims the benefit is each of said earlier-filed U.S. applications that form an unbroken chain of continuing or continuation-in-part applications and of their respective provisional applications.

FIELD

This patent specification relates to medical imaging. More particularly, this patent specification relates to breast ultrasound imaging using chestward compression of a breast and automated scanning with a transducer integrated with a radial scanning template.

BACKGROUND

Automated breast ultrasound scanning systems, generally referred to as "ABUS", have been developed for mass screening and are intended to be operated by medical technicians or certified nurses on asymptomatic patients, with the results read by physicians later. This operating procedure is similar to operating a screening x-ray mammography machine, where image acquisition is performed with lower-cost personnel and the results are interpreted by physicians later. These ABUSs have been commercially introduced for a number of years and over a thousand of such units are believed to be in active use worldwide.

Some such ABUSs are operated with patients in a supine position (patient facing up with her back on the table) and some are operated with patients in a prone position (patient facing down with her chest on the table).

The known supine ABUSs are quite slow and may lack sufficient patient throughput for low-cost screening purposes. The known supine ABUSs require multiple number of scans over each breast to cover the whole breast; some breasts require 2 scans and some larger breasts may require 5 scans.

The prone ABUSs are faster with a one-size-fits-all design. See, for example, https://www.youtube.com/watch?v=RgEYWpzLtrk. This design suffers frequent patient positioning problems as well as breast contact problems, because the operator cannot see the breast as it is making contact with the scanning device and positioning is done "blind". Sometimes, these positioning and contact problems cause the scan to miss significant parts or even the most important parts of the breast such as the upper outer quadrant where 50% of the breast cancers generally reside. The known prone ABUSs are also poor in stabilizing the breast during scanning, resulting in poor 3D reconstruction and poor CAD results (computer analysis detection and diagnosis, which is usually computed from 3D volumetric data).

Another issue for known ABUSs, supine or prone, is nipple pain as well as poor image acquisition in the nipple area. Pain of different levels is experienced by patients as the transducers scan over the nipple. In some cases, the acquisition process can be very painful. Furthermore, the bump in scanning caused by the nipple can frequently make the nipple area not readable in known ABUS images, with the possibility of missing some cancers under the nipple. The nipple bump can frequently cause distortions in 3D reconstruction and thus can result in poor CAD results.

Poor image acquisition, due to patient motion or poor breast contact, and poor positioning, are usually discovered when the physicians are reading the results, after the patients have been discharged. Thus, if problems are discovered, the patient must be called back for another exam. This can cause a substantial increase in cost to the screening process in addition to the inconvenience to patients.

Yet another significant issue with known ABUSs is that areas under the nipple and axilla areas are frequently missed or inadequately acquired. Missing these areas could result in as much as 20% or more of the cancers being missed. Again, the patient may have to be called back for another examination.

SUMMARY

Some embodiments comprise an automated system for scanning a patient's breast with ultrasound, comprising: a scanning pod including a housing and a membrane that is secured to one side of the housing, transmits ultrasound, and is permeable to coupling gel, a scanning template mounted in or to the housing to rotate relative to the membrane and having a nipple hole, wherein said template is essentially planar or has an opening angle of more than 150 degrees or a radius of more than 20 cm, at least one transducer radially extending outwardly from the nipple hole and integrated with the template to rotate therewith, and a motor configured to rotate the template and the at least one transducer relative to the membrane; wherein said scanning pod is configured to press the patient's breast with said membrane toward the patient's chest wall to thereby at least partly flatten the breast, with the breast's nipple in the nipple hole of the template; wherein said at least one transducer is configured to make ultrasound contact with the breast through the membrane and coupling gel permeating the membrane when the scanning pod is pressing the breast, and to rotatably scan the breast with said at least one transducer by rotating the template to thereby generate plural, radially oriented, original two-dimensional (2D) images of the breast; a computer processing system configured to receive said 2D original images and to process them into at least one three-dimensional (3D) image of the breast and other images of the breast; and a display coupled with the processing system to display said images.

The membrane can have a nipple opening aligned with said nipple hole in the template, wherein the breast's nipple protrudes through said nipple opening and nipple hole while the template rotates and the at least one transducer is in ultrasound contact with the breast. In some embodiments, the membrane faces down to press the breast of a patient who is on her back or side down against the patient's chest wall but in other embodiments the membrane faces up, to press up the breast of a patient who is lying face down against the patient's chest wall, in which case the system can further include a patient table, wherein said scanning pod faces up at a portion of the table configured to receive the patient's breast when the patient is face down on the table.

The system can further include a camera having a field of view that includes the nipple hole and at least a substantial portion of the breast, and wherein each of the template and the membrane is transparent or at least translucent. Each of the membrane, the template, and at least a portion of the housing can be sufficiently transparent to allow visual observation of the breast and the degree or wetness of the contact between the breast, membrane and template.

The template has an opening angle of more than 160 degrees, or more than 165 degrees, or more that 170 degrees, of the opening angle can be more than 175 degrees and therefore the template may be deemed essentially flat.

Some embodiments comprise an automated system for imaging a patient's breast with ultrasound, comprising: a rotary template and at least one ultrasound transducer integrated therewith and radially extending from a central area of the template; said rotary template having an opening angle of at least 150 degrees or being curved with a radius of curvature of at least 20 cm; a motor configured to rotate the template; a membrane wettable with ultrasound couplant gel and shaped and dimensioned to be at least co-extensive with the template; a mounding mechanism supporting the template and membrane, wherein when the membrane presses chestwardly against the patient's breast with sufficient force, the membrane is in physical contact with the breast and the template and the at least one transducer are in physical contact with the membrane; wherein rotation of the template relative to the membrane and the breast with said motor causes the at least one transducer to scan the breast in a rotary motion and generate a multiplicity of original, two-dimensional (2D) images of breast slices extending along respective radially oriented planes.

The rotary template has a nipple hole in a central area thereof, in which the breast's nipple extends during said scan with said at least one transducer. The membrane can also have a nipple opening aligned with the nipple hole in the template, wherein the breast's nipple extends in said nipple opening and nipple hole during said scan with said at least one transducer. The scanning template and at least one transducer can remain laterally spaced from the breast's nipple during said scan. The at least one transducer can be configured to emit an ultrasound beam that spreads laterally into an area under the breast's nipple during said scan, and can be configured to operate in the frequency range of 5-16 MHz. The template and membrane are transparent or at least sufficiently translucent to allow visual observation of physical contact between the breast, membrane, and template. The system can include a pressure gauge configured to show the pressure said membrane and/or template exert on the patient's breast. A camera can be included in the mounting structure, together with a display showing the relative positions of the membrane, template, and breast during said scan and/or in preparation for the scan. The system can further include a table on which the patient lies during said scan, wherein said mounting mechanism moves down to have the membrane make contact with the breast, or the system can include a table on which the patient lies face down to have the breast press against said membrane in a downward motion.

An automated method can be provided for imaging a patient's breast with ultrasound, comprising: compressing the breast with one side of a membrane that permits transmission of ultrasound therethrough and is permeable to ultrasound couplant, and pressing the other side of the membrane with a rotary template that has at least one radially extending ultrasound transducer integrated therewith; positioning the breast's nipple in a nipple hole in the template and a nipple opening in the membrane aligned with said nipple hole; driving the template with a motor to rotate the template and said one or more transducers relative to the membrane and the breast; generating original, two-dimensional (2D) ultrasound images from outputs of said one or more transducers, which images conform to respective radially oriented planes; and processing the original 2D images into other images of the breast and displaying selected ones of said original and other images.

DETAILED DESCRIPTION

Figure 1:
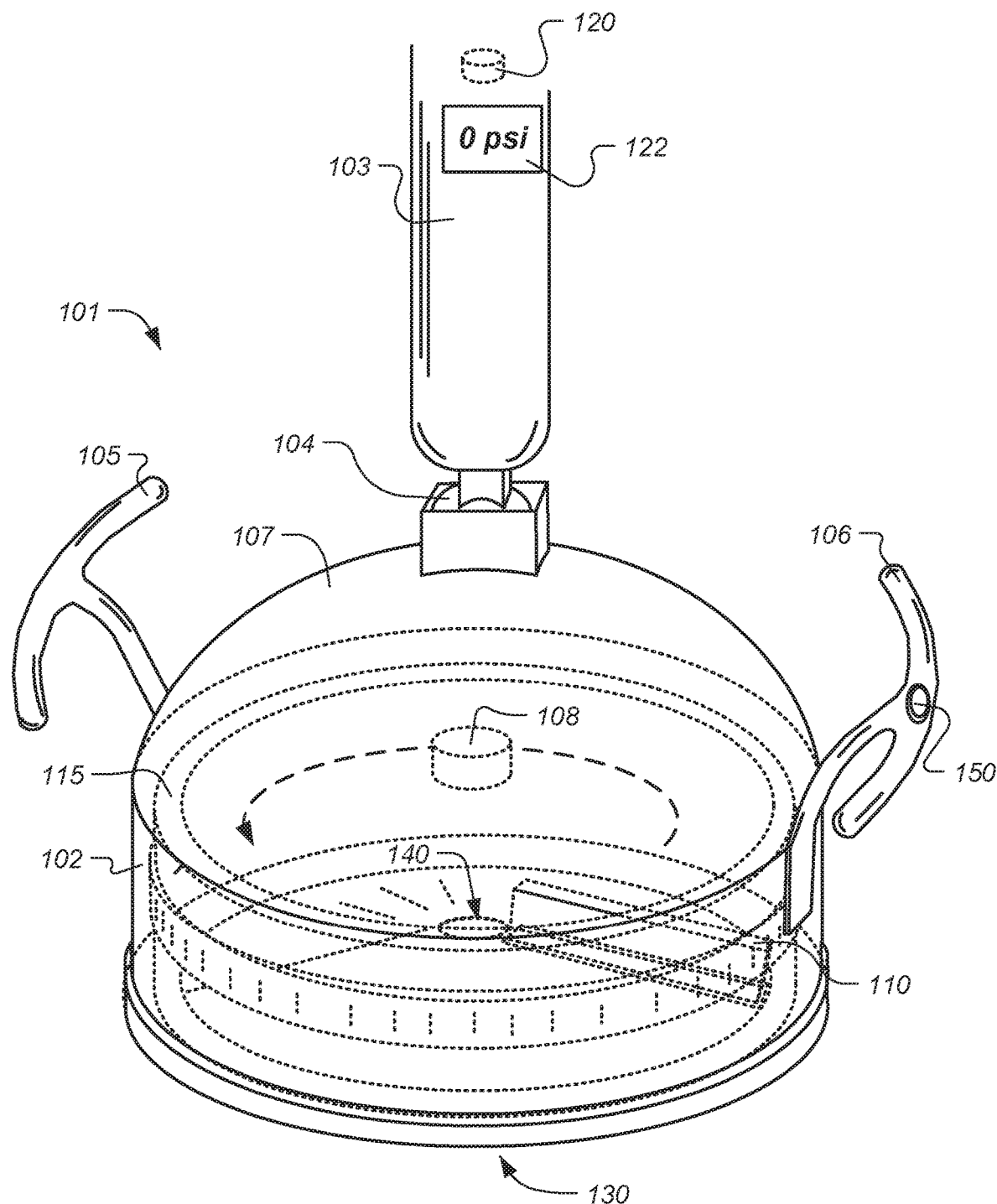
FIG. 1 is a perspective view showing some aspects of a breast ultrasound scanning device and related methods, according to some embodiments.

According to some embodiments, a rotary ABUS scanning systems and related methods are described which address patient throughput and some or all of the aforementioned drawbacks associated with screening of asymptomatic patients with known conventional ABUSs systems. According to some embodiments, a rotary scanner is provided that can be used in diagnostic procedures on symptomatic patients, i.e., those who were found with abnormalities in prior examinations or by patients themselves, in addition to or instead of screening asymptotic patients.

In some embodiment, an apparatus and related methods for scanning the breast with ultrasound are provided. The apparatus includes a patient table on which the patient can be positioned supine (facing up) or partly on her side, and an ultrasound scanning pod mounted on an arm of an ultrasound machine. The ultrasound machine operates an ultrasound transducer in the pod and processes the scanned images. A display system is configured to display the images of scanned slices, a quick reconstructed 3D image, images of coronal slices, and other system information or status to technician/operator. In some embodiments, the display system also shows images of additional scans by hand-held ultrasound transducers on areas of the axilla and under the nipple. In some embodiments, the display system shows patient positioning and patient compression images/information. A technician/operator places the scanning pod by chestwardly compressing the pod on the patient's breast while the patient is supine or partly on her side on the table. Once desirable compression is achieved, in some cases displayed to the technician/operator as measured by a pressure sensor, the operator may lock the position of the scanning pod for the duration of scan, which typically lasts from 30 seconds to 90 seconds per scan. The scanning pod has a high-frequency (operating in the range of 5-17 MHz) ultrasound transducer mounted on a rotating template inside the pod. The scanning pod includes a driving mechanism that is configured to rotate the template to scan the breast. The rotating template preferably is made of substantially transparent or translucent material so that the technician/operator can observe the extent of the "wetting of the breast" to achieve good positioning and contact with the breast. The contact of the breast, covered with the usual ultrasonic gel couplant, with the rotating template, preferably is observable to confirm that the breast is in wet contact with the template. A good contact would show that the wet area has no air bubbles. A good positioning would show that the wetted area is indeed the desired parts of breast to be scanned. The template can have a hole at a central area for the breast's nipple. The template can be substantially flat, or essentially planar, or can be conically shaped with a conic angle of more than 150 degrees, or more than 160 degrees, or more than 170 degrees. When the angle is more than 175 degrees but no more than 180 degrees, the template can be considered substantially flat or essentially planar. In some embodiments, the template is slightly curved, with the radius of curvature preferably more than 20 cm, or preferably more than 30 cm or more. The radius of curvature can be relatively large for scanning pods for larger breasts, so that the compressed breast thicknesses are be more uniform in the entire scanning area. This insures good and more uniform penetration with high-frequency ultrasound. The quality of ABUS images is influences by the frequency range of the transducer used, which in turn is dependent on the breast thickness to be scanned. Hooley et al (in "Breast Ultrasonography: State of Art", Radiology Vol. 268 (2013), pp. 642-659), incorporated herein by reference, states that 5-17 MHz frequency range should only be used on breast thickness of less than 3 cm, while much lower frequency range of 5-12 MHz is suitable for thicker breasts of 5 cm or more.

Figure 8:
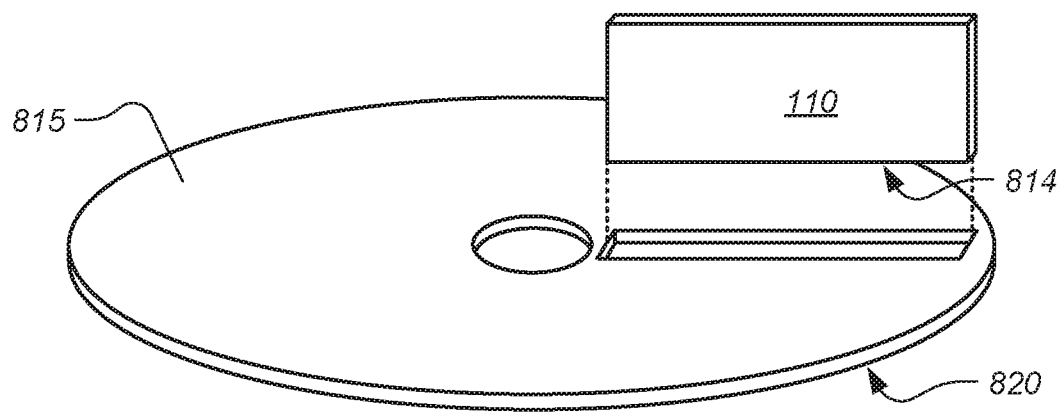
FIG. 8 is a perspective view illustrating a transducer mounted on a substantially flat scanning template, according to some embodiments.

According to some embodiments, the scanning template is substantially flat, or essentially planar, especially for larger breasts. An example of a substantially flat or essentially planar scanning template is shown in FIG. 8. The optimum number of slices per one rotational scan can be approximately 1,000. These slices are two-dimensional original ultrasound images of thin breast slices that are along radially oriented planes in the breast. According to some embodiments, fewer slices may be used as a pre-scan to facilitate a quick reconstruction of coronal slices to show to the technician/operator that there are no positioning, or contact, or tissue pulling errors. Such quick reconstruction of coronal slices can be quite beneficial since those types of scanning errors are often difficult to detect on 2D scanned images. In addition or instead, a quick 3D image of the breast can be reconstructed from fewer than all slices, and displayed to the operator.

According to some other embodiments, the transducer/template rotates over a membrane that can be a fabric or mesh, which remains stationary during the scan and covers and holds the breast, so that the rotating template does not cause pulling of breast tissue. The membrane can be covered or permeated with the usual ultrasonic gel couplant to ensure good ultrasound contact between the transducer and the breast. Breast contact is indicated by the extent of the wetting of the breast with the couplant under visual observation, as the scanning pod is chestwardly compressed onto the breast. Both the membrane and the ultrasonic gel not only should be substantially ultrasonically transparent but also should be substantially transparent or translucent visually so that wetting of the breast can be observed by the technician/operator to achieve good positioning and contact with the breast. Said membrane, fabric or mesh, may be disposed of after one or a few uses, for sanitary reasons.

In some embodiments, the nipple protrudes through a central hole in the membrane and the scanning template, so that the transducer would not scan across the nipple. This would allow easier patient position, and also removes nipple pain and nipple bump during scanning, which is a major problem of known current ABUSs, supine or prone. According to some embodiments, a hand operated transducer is provided in addition to the transducer(s) in the pod, so that the operator can manually scan the nipple area plus the axilla area, which are frequently missed or poorly acquired by conventional ABUS techniques, and can scan any other area. These hand scanned images can then be added to the final display for the physicians.

According to some embodiments, a wide-angle camera is provided on or within the scanning pod to further ensure good positioning and contact with the breast. This feature is particularly beneficial for prone ABUS arrangements, where conventional positioning is typically done unaided or "blind".

In some embodiments, quickly reconstructed 3D images, and thick slice coronal images, are shown on a display screen at the scanning unit to the operator to assure the operator that the image acquisition is satisfactory, i.e. no patient motion, scanning pod slippage and positioning or contact or tissue pulling problems. In some known conventional ABUS techniques, only 2D images are displayed to the operator. These 2D images may be insensitive to breast distortions, positioning and contact errors, and patient motion. Breast distortions and patient motion can result in poor coronal images and poor CAD (computer-aided diagnosis and detection) results. The quick reconstruction can be made with lower spatial resolution involving fewer scan slices than the typical 1,000 or so slices.

In some embodiments, a multiple number (two or more than 2) rotary scanning pods are provided in a single rotary scanning system. Providing multiple scanning pods, each having different sizes, with transducers operating at different high-frequency ranges, can improve positioning and contact for a wide range of different breast sizes.

All of the embodiments described herein can be applied to supine type ABUS systems as well as to prone type ABUS systems in which the patient is lying face-down on a table and the scanning pod is below the patient's breast.

Similar to the supine ABUS discussed above, multiple number (more than one) of differently sized or shaped scanning pods can be included in a prone system, with transducers operating at different high-frequency ranges. Such plural scanning pods can be provided on the same patient table to cover breasts of different sizes. For additional scans with the hand-held transducer, the patent can turn over on her back or side.

This rotary scanner, although designed specifically for breast cancer screening of asymptomatic patients, could perform diagnostic examinations on symptomatic patients. Some special diagnostic techniques, such as "elastography", "microbubble contrast imaging", "color Doppler" and "contrast subtraction imaging" could also be performed with this rotary scanner. Such techniques are known for conventional ultrasound breast imaging, with devices other than the rotary scanning described in this patent specification. For elastography, the simplest procedure is to acquire the breast images twice, each time with different degrees of compression. The incompressibility or lack of changes in the simple ratio of the longest axis over shortest axis of a lesion gives a good indication of the lesion's malignancy. This simple measure is difficult with 2D images, especially as the malignant lesion, which is not very compressible, frequently slips under compression, yielding erroneous 2D compressibility results. More sophisticated elastography involves vibrating or otherwise inducing motion of the breast and observing differences in response to breast motion between suspected lesions and other breast tissue.

FIG. 1 is a perspective view showing some aspects of a breast ultrasound scanning device and related methods, according to some embodiments. The apparatus of FIG. 1 includes an ultrasound scanning pod 101 which has an outer housing 102. A rotating ultrasonic transducer 110, mounted on or integrated with a rotating template 115, is provided inside housing 102 and is driven by a driving mechanism. Two transducers can be used at the same time, to extend over the entire diameter of the breast to thereby scan the entire breast (possibly omitting the nipple) in half a rotation (plus a small overscan angle), or more than two transducers can be used at the same time. The scanning pod 101 is held by a supporting arm 103 through a ball joint 104. The pod 101 can be positioned over the patient's breast by the operator using the attached handles 105 and 106. According to some embodiments, a locking mechanism and a pressure gauge 120 are installed on the supporting arm 103 so that the scanning pod 101 can be locked in place using locking button 150 once satisfactory positioning and contact have been achieved. Readings from pressure gauge 120 can be displayed on pressure indicator display 122 to inform the operator that a desired pressure has been achieved in the chestward compression against the breast. The top cover 107 of housing 102 can be made of a transparent material to allow the operator to visually guide the positioning of pod 101 onto the patient's breast. According to some embodiments, a wide-angle camera 108 is located on the top cover 107 or elsewhere within pod 101, preferably in the center, to further aid the operator in the positioning of the scanning pod 101 on the patient's breast. This camera 108 is particularly beneficial for prone type of ABUS systems described in more detail below, since the operator does not have a good view of the breast while the patient is being positioned face down. The rotary transducer 110 rotates over a fabric membrane 130, which is transparent to ultrasound and permeable to couplant gel, which membrane covers and holds the breast while remaining rotationally stationary relative to the housing 102 and the breast during scanning. This configuration has been found to ensure that the rotating template does not cause pulling of breast tissue. During operation, the fabric membrane 130 is typically covered and permeated with ultrasonic gel couplant to ensure good ultrasound contact between the transducer and the breast. According to some embodiments, the fabric membrane 130 is replaceable. Breast contact can be indicated by the extent of the wetting of the breast under visual observation, as the scanning pod 101 is chestwardly compressed onto the breast. Both the fabric membrane 130 and the ultrasonic gel coating not only should be substantially ultrasonically transparent but also should be visually transparent so that good positioning and contact with the breast can be observed and achieved by the technician/operator. The transducer 110 is mounted on a transparent or at least translucent template 115. According to some other embodiments, template 115 is not in direct contact with the breast, so that the transducer 110 rotates over the fabric membrane 130 which covers and holds the breast. A fabric membrane without a template is used in known supine ABUSs on the market as well as in a rectilinear scanner discussed in U.S. Pat. No. 7,731,662, which is incorporated herein by reference. According to many of the embodiments disclosed herein, the template 115 preferably is in direct contact at all points with the fabric membrane 130 and helps the membrane 130 better hold the breast during the scan. The embodiments disclosed herein differ from those in U.S. Pat. No. 7,731,662 in several important ways. In the embodiments disclosed herein, a rotary transducer template, carrying the transducer, reduces breast motion during scanning. In some embodiments disclosed herein, a small nipple hole is added to the fabric membrane to allow the nipple to protrude through the holes in both the scanning template and the fabric membrane to prevent nipple pain and avoid image artifacts due to passage of the transducer over the nipple. In the embodiments disclosed herein, the fabric membrane is preferably light in color, or substantially optically translucent when coated with ultrasonic gel, so as to allow good visibility of the breast contact. This is particularly beneficial in the prone ABUS systems disclosed herein. A nipple hole 140 is provided in the center of the scanning template 115 to allow the nipple to protrude through the central hole. A matching hole or opening is provided in the fabric membrane 130, so that the transducer does not scan across the nipple. This reduces nipple pain during scanning, which is a major drawback of known conventional ABUS systems. According to some embodiments, a hand operated transducer (not shown in FIG. 1) is provided so that the operator can manually scan the nipple area plus the axilla area, which are frequently missed or poorly acquired by most conventional ABUS systems, and/or can scan other areas. These hand scanned images can then be added to the final display for the physicians or other personnel.

Figure 2:
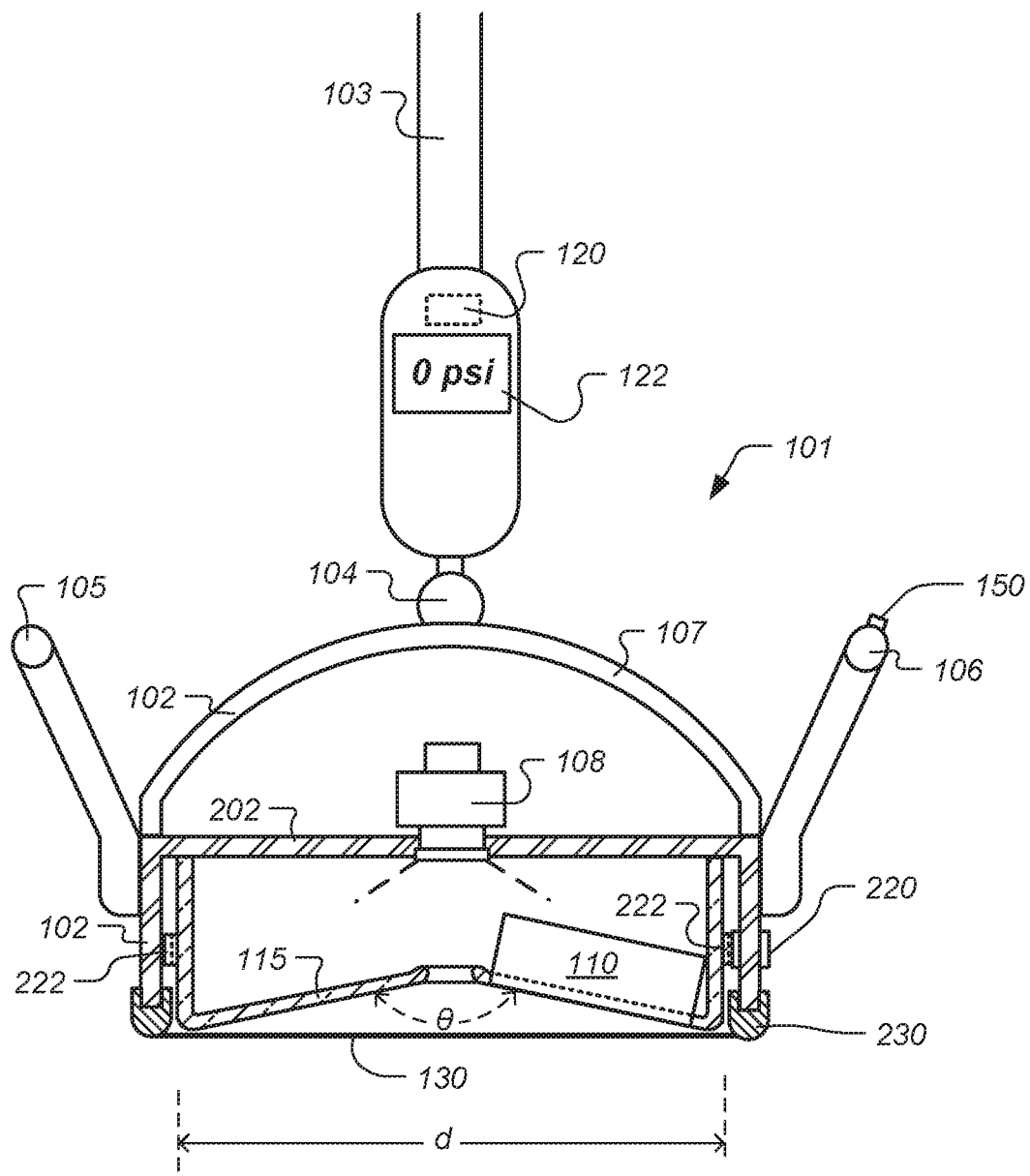
FIG. 2 is a cross-section view illustrating further aspects of a breast ultrasound scanning device and related methods, according to some embodiments.

FIG. 2 is a cross-section view illustrating further aspects of a breast ultrasound scanning device and related methods, according to some embodiments. In this case, the outer housing 102 made up of lower housing 202 and upper housing 107. Within lower housing 202 is rotating template 115 on which rotating transducer 110 is mounted. A peripheral motor 220 has gears that engage teeth 222 that are mounted on a circumferential strip secured around the outer edge of template 115. Motor 220 is thus configured to rotate the template 115 and transducer 110. Also shown in FIG. 2 is membrane fabric 130 which is mounted to the lower housing 220 using ring 230, such as a snap-ring. When compressing the breast, the membrane 130 and the breast surface are both pushed against the rotary template 115. According to some embodiments, the diameter d of the rotating template 115 is between 15 and 25 cm and preferably is approximately 20 cm, although other dimensions can be chosen. According to some embodiments, the lower surface of template 115 is cone-shaped, with a cone angle θ of at least 150 degrees, or at least 160 degrees, or at least 170 degrees, or at least 175 degrees. Or, the cone angle is more than 175 degrees but no more than 180 degrees, in which case the template is deemed substantially flat or essentially planar. In some cases, the template can be completely flat (cone angle 180 degrees), or nearly so. According to some embodiments, the lower surface of template 115 can be curved or spherical in shape and can have a radius of curvature of at least 20 cm, or at least 30 cm, or more.

Figure 3:
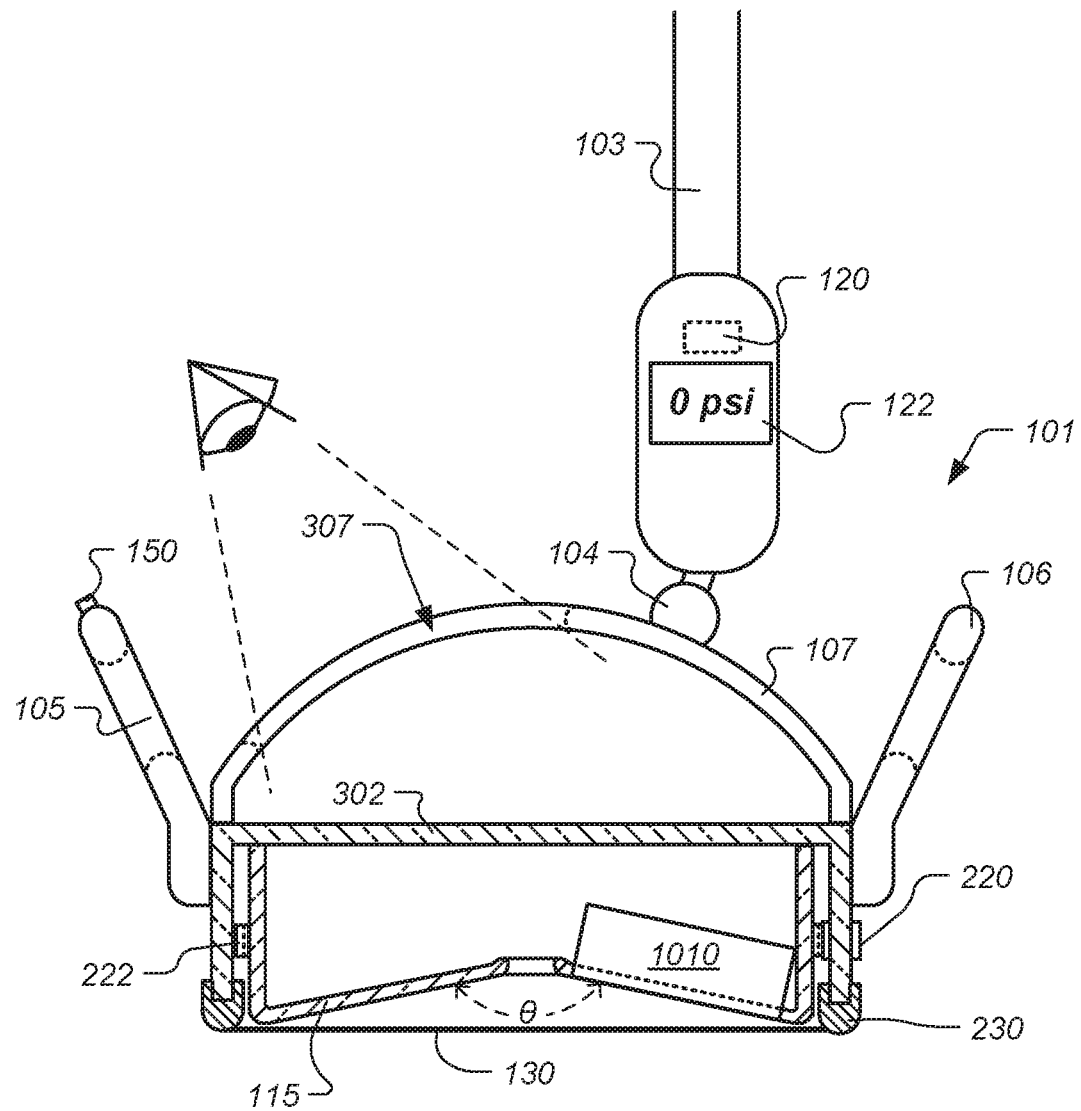
FIG. 3 is a cross-section view illustrating further aspects of a breast ultrasound scanning device and related methods, according to some other embodiments.

FIG. 3 is a cross-section view illustrating further aspects of a breast ultrasound scanning device and related methods, according to some embodiments. In this case, the upper housing 107 includes a viewing window 307 that allows for improved ability to visually guide the pod 101 so it is correctly positioned on the breast. In this case, at least the upper portion of lower housing 302 is transparent to allow adequate viewing. This arrangement shown offers improved simplicity for supine rotary ABUS systems. According to some embodiments, the support arm 103 and ball joint 104 can be mounted in an offset fashion as shown so that the operator can better visually guide the breast positioning and achieving optimal breast contact. According to some embodiments, instead of providing a window 307, a portion or all of the upper housing 107 can be made of transparent material.

Figure 4A:
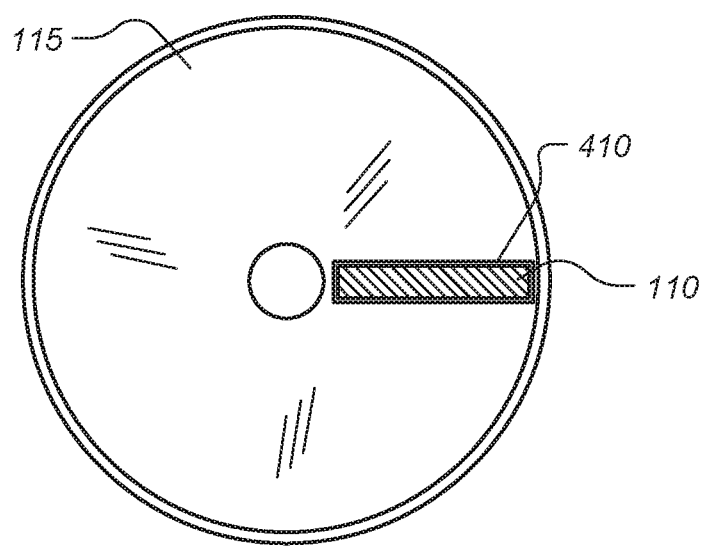
FIGS. 4A and 4B are a top view and perspective view, respectively illustrating further aspects of a breast ultrasound scanning device and related methods, according to some other embodiments.
Figure 4B:
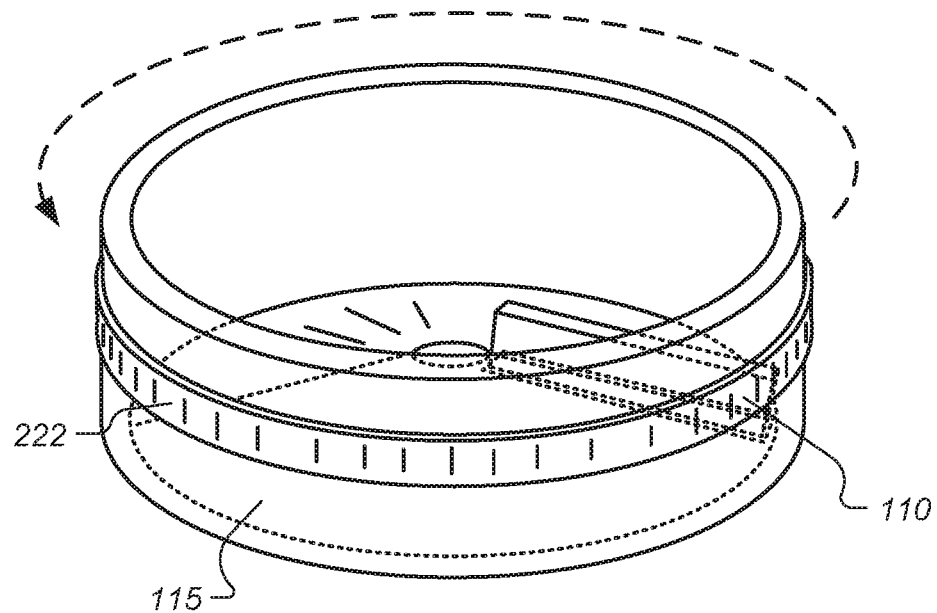

FIGS. 4A and 4B are a top view and perspective view, respectively, illustrating further aspects of a breast ultrasound scanning device and related methods, according to some embodiments. The rotating template 115 and transducer 110 are shown. As seen in FIG. 4A, a window or opening 410 is formed in template 115 that allows transducer 110 to the securely held to the template. The lower surface of the transducer 110 is flush with the lower surface of template 115, or nearly flush. In FIG. 4B, the circumferential teeth 222 are also illustrated.

Figure 5A:
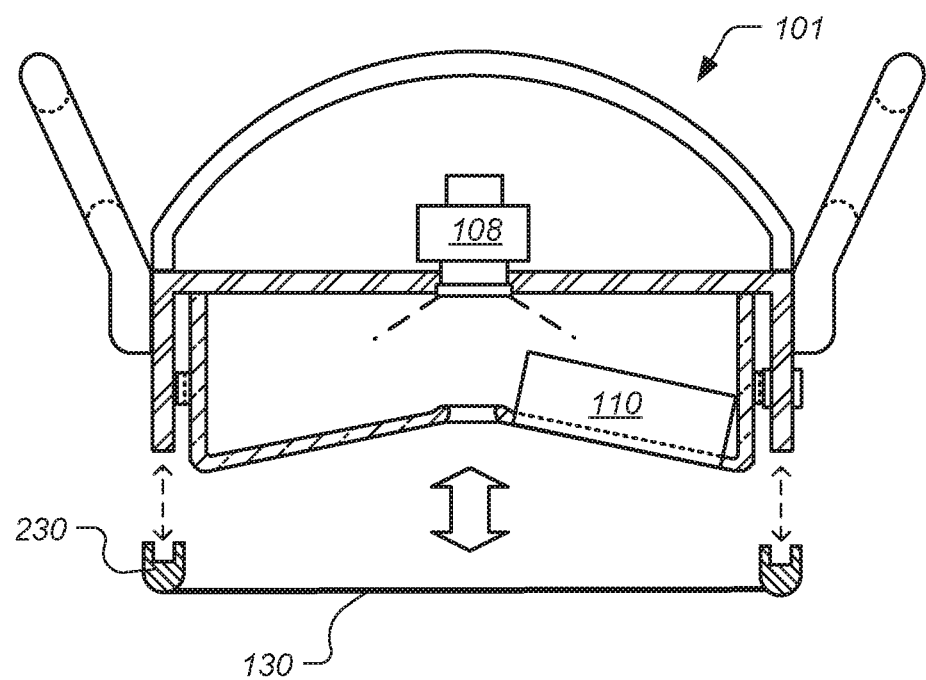
FIGS. 5A-D are cross section views illustrating further aspects of a breast ultrasound scanning device and related methods, according to some other embodiments.

FIGS. 5A-D are cross section views illustrating further aspects of a breast ultrasound scanning device and related methods, according to some embodiments. FIG. 5A shows that, according to some embodiments, the membrane fabric 130 and holding ring 230 are configured to detach from pod 101, thereby facilitating easy replacement of membrane fabric 130 after each use, or after a few uses. According to some embodiments, the membrane fabric 130 is replaced each time the pod 101 is used for a new patient.

Figure 5B:
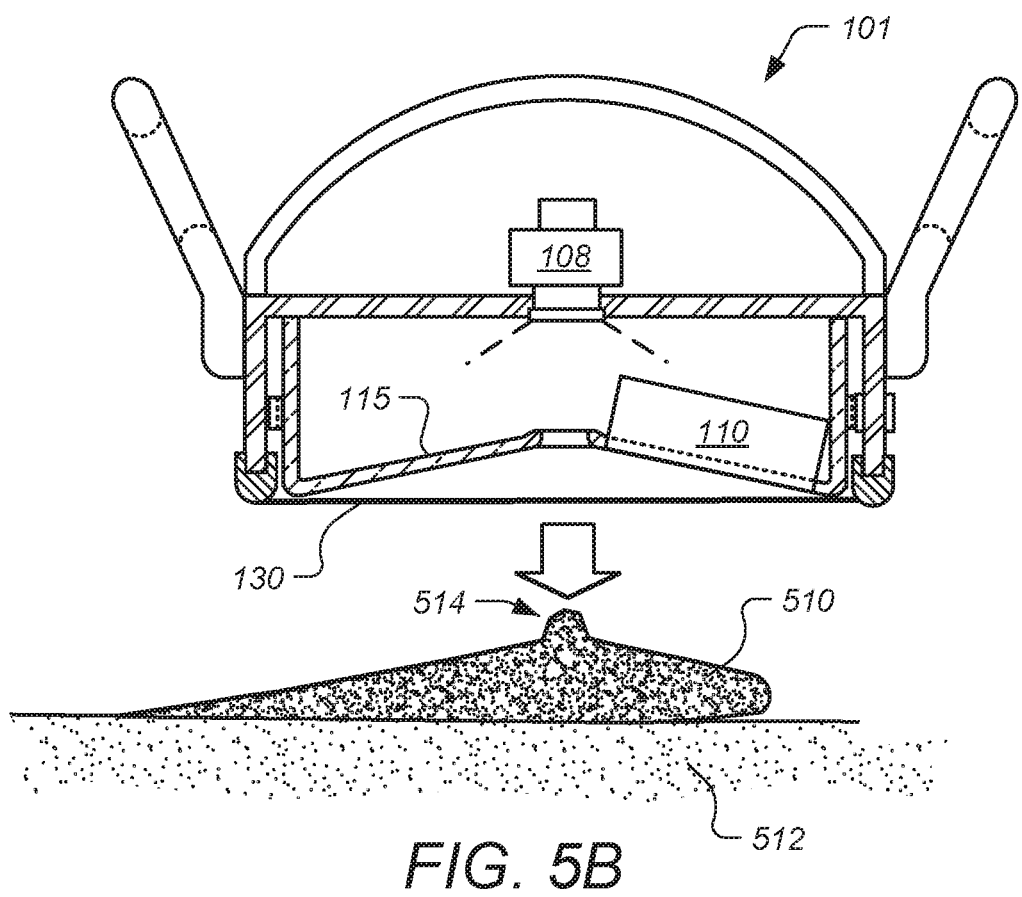
Figure 5C:
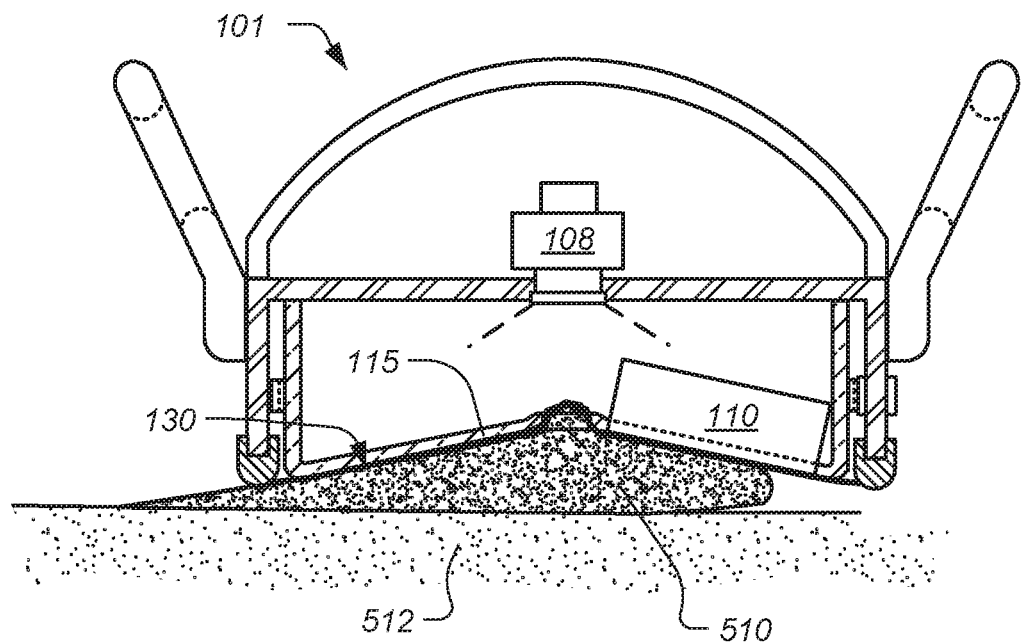
Figure 5D:
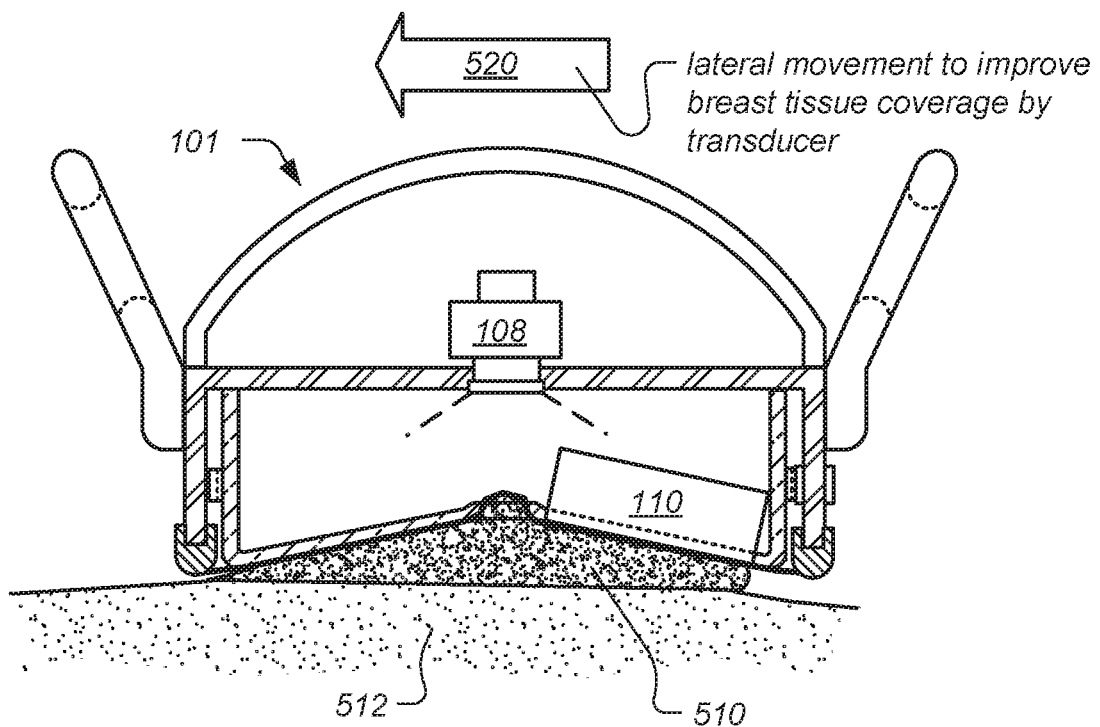

FIGS. 5B and 5C show the relationship of the scanning pod 101, scanning template 115, transducer 110 and replaceable membrane fabric 130, and the breast tissue 510, chest wall 512 and nipple 514. In the case of FIG. 5C, the pod 110 is poorly positioned over the breast since the transducer 110 would be missing a good portion of the breast and potentially missing detecting cancers. An image resulting from the poor positioning shown in FIG. 5C would have an undesirable artifact known as a "crescent moon." FIG. 5D shows that by moving and repositioning the scanning pod a better positioning is achieved. In this case the lateral movement shown by arrow 520 improves breast tissue coverage by transducer 110.

Figure 5E:
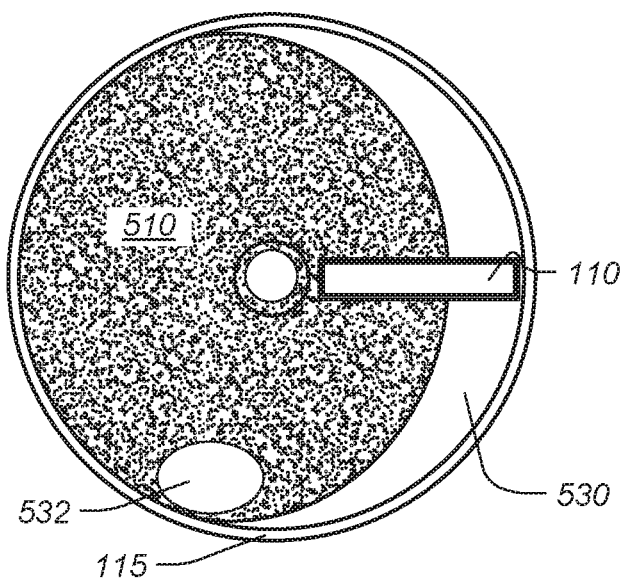
FIGS. 5E and 5F are top views illustrating further aspects of a breast ultrasound scanning device and related methods, according to some other embodiments.
Figure 5F:
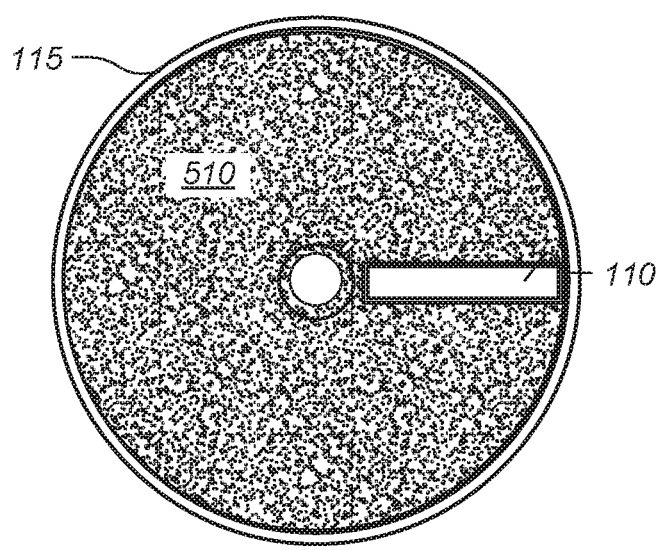

FIGS. 5E and 5F are top views illustrating further aspects of a breast ultrasound scanning device and related methods, according to some embodiments. These FIGS. illustrate aspects of a view that could be observed by an operator during placement of pod 101 (as shown in FIGS. 1-3) on a patient's breast. The technician/operator can observe the extent of the "wetting of the breast" to achieve good positioning and contact with the breast. The contact of the breast, covered with the usual ultrasonic gel couplant, with the rotating template, is observable to see if the breast is in wet contact with the template. A good contact would show that the wet area has no air bubbles. A good positioning would show that the wet area is indeed the desired parts of breast to be scanned. The view might be observed through a window or transparent/translucent portions of the scanning pod, e.g. as shown in FIG. 3, or it might be observed real-time on a display as captured by a camera, e.g. as shown in FIGS. 1 and 2. FIG. 5E illustrates a poorly positioned pod since it includes a "crescent moon" region 530 as well as an air bubble 532. Such poor positioning is easily detected by the operator either by live view or view on a display. FIG. 5F shows a view that might be observed when there are no longer any pod positioning issues or air bubbles that can deteriorate and image, and a high quality ultrasonic image can be obtained.

Figure 6:
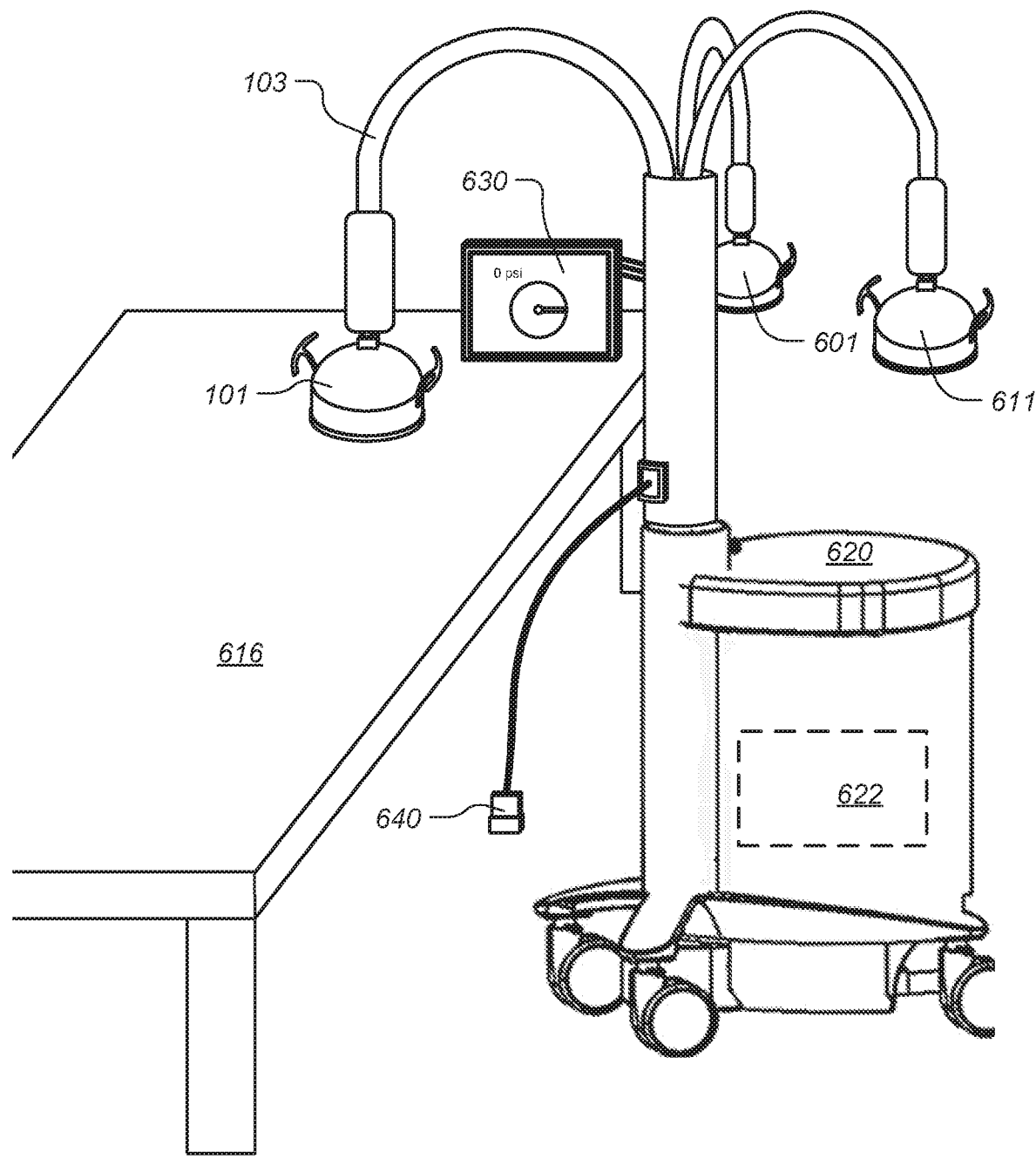
FIG. 6 shows various components of a breast ultrasound scanning system configured to scan patients in a supine position, according to some other embodiments.

FIG. 6 shows various components of a breast ultrasound scanning system configured to scan patients in a supine position, according to some embodiments. The patient lies supine on table 616. As shown, the scanning pod 101 can be attached via support arm 103 to a cart 620. Cart 620 also includes a display 630 and a computer processing system 622. Display 630 can be used to show the operator live view from an internal camera (e.g. camera 108 shown in FIGS. 1 and 2), compression information (e.g. from sensor 120 shown in FIGS. 1-3), and/or images of additional scans by hand-held transducer 640 on areas of axilla and under the nipple or other areas. According to some embodiments, display 630 is also configured to display the images of scanned slices, results of a quick reconstructed 3D image, coronal slices, and/or other system information or status to the technician/operator. FIG. 6 also shows two additional scanning pods 601 and 611 provided on cart 620. Pods 101, 601 and 611 can be different sizes and therefore the scanning system can be used or optimized to accommodate a wider range of breast sizes.

For scanning in the prone (patient facing down) position, the scanning pod can be embedded or otherwise secured in or to the patient table in a suitable relationship with the surface of the table. In these embodiments, a wide-angle camera can beneficially be used to guide the operator in placing the patient properly such that the patient's nipple protrudes through the nipple hole (and the aligned opening in the membrane) and further in positioning the breast properly by observing the extent of the wetting of the breast. According to some embodiments, further positioning adjustments can be provided by having a slightly (few cm in x and y direction in the plane of the table top) movable and lockable table top and/or by moving the table top manually. According to some embodiments, the scanning pod is fixed relative to a table base rather the table top. Further positioning could be performed by a slightly (few cm in x and y direction in the plane of the table top) movable scanning pod relative to the table top, operated manually or electronically. In some embodiments, the movable scanning pod could also be moved in the z (up and down) direction to improve compression. A pressure sensor and a pressure indicator can be added to inform the operator of the degree of compression.

Figure 7A:
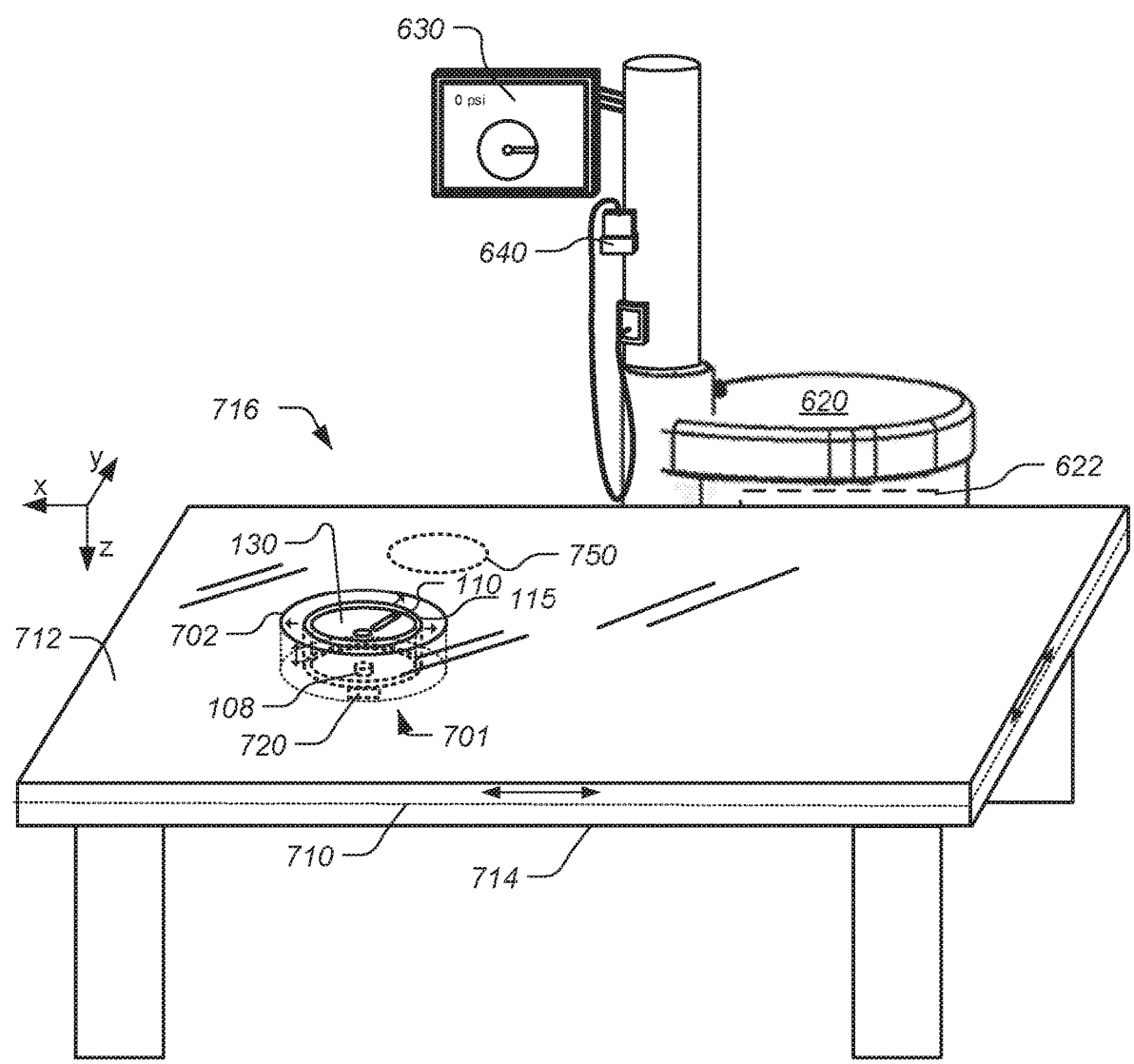
FIGS. 7A and 7B shows various components of a breast ultrasound scanning system configured to scan patients in a prone position, according to some other embodiments.
Figure 7B:
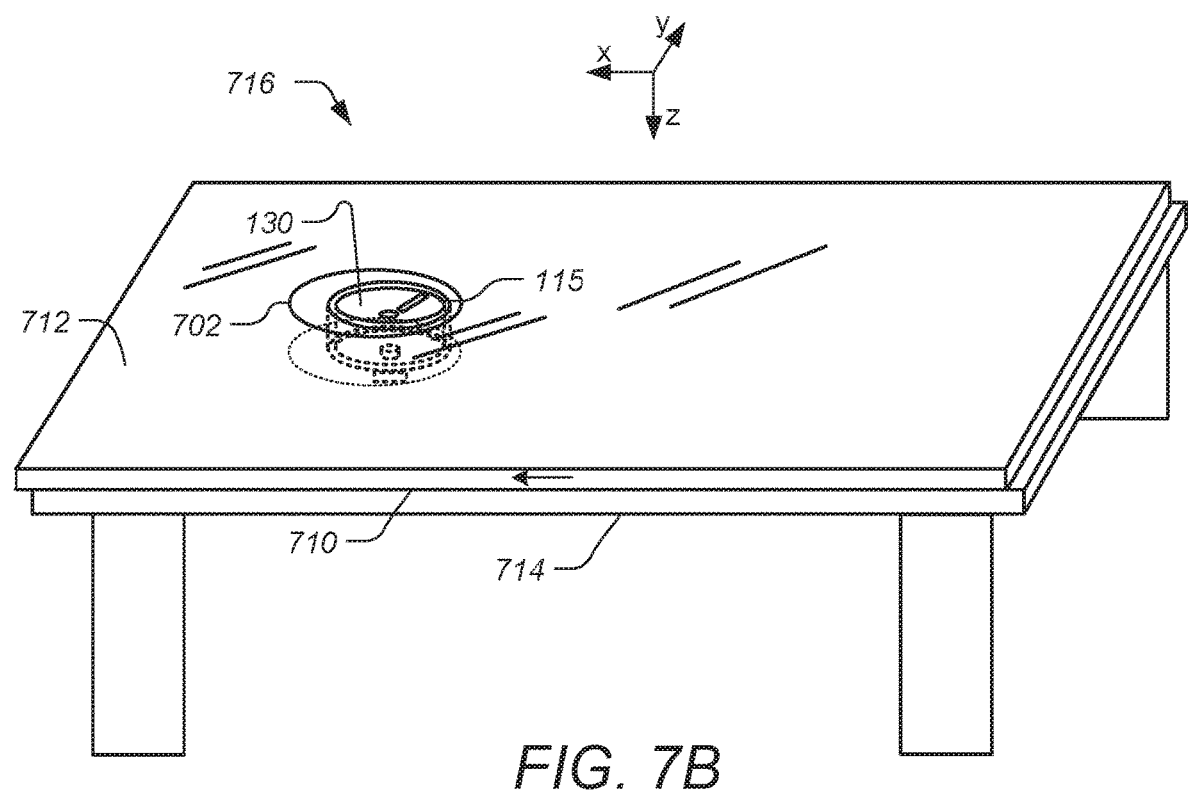

FIGS. 7A and 7B shows various components of a breast ultrasound scanning system configured to scan patients in a prone position, according to some embodiments. Scanning pod 710 is mounted on or to the table 716 to scan patients lying in a prone position. In this case, rotating template 115, transducer 110, membrane fabric 130 and camera 108 are mounted within a housing cavity 702 formed in or secured to table 716. According to some embodiments, the mounting allows for movement of the scanning pod in x, y and/or z (vertical) directions relative to the surface of table 716. Such relative movement allows the operator to achieve better positioning. According to some embodiments movement mechanisms, not shown, are provided that move the scanning pod relative to the table or a portion thereof. According to some embodiments, the table 716 is formed of an upper portion 712 and lower portion 714. The scanning pod 701 is mounted so as to remain fixed in the x and y and optionally z directions relative to the lower portion 714. The upper portion 712 is configured to move in the x and y and optionally z directions relative to the lower portion 714. FIG. 7B shows the upper portion 712 moved in the x direction relative to the lower portion 714 and scanning pod 701. According to some embodiments additional scanning pods can be provided, e.g. pod 750, that is a different size and/or shape than pod 701 to accommodate different size breasts, and moved into position to replace pod 701 as needed. Also shown in FIG. 7A is cart 620 that includes display 630, processing system 622 and hand held transducer 640. According to some embodiments, hand held transducer 640 is used to scan the axilla area and/or the nipple area or other areas while the patient is lying in a supine position or in other positions.

FIG. 8 is a perspective view illustrating a transducer mounted on a substantially flat or essentially planar scanning template 815, according to some embodiments. Transducer 110 is shown mounted through a slot in the scanning template 815. When mounted, the surface 814 of transducer 110 preferably is flush or nearly flush with the lower template surface 820. This configuration allows the template to better compress the breast and help the fabric membrane in further holding the breast in place.

Figure 9A:
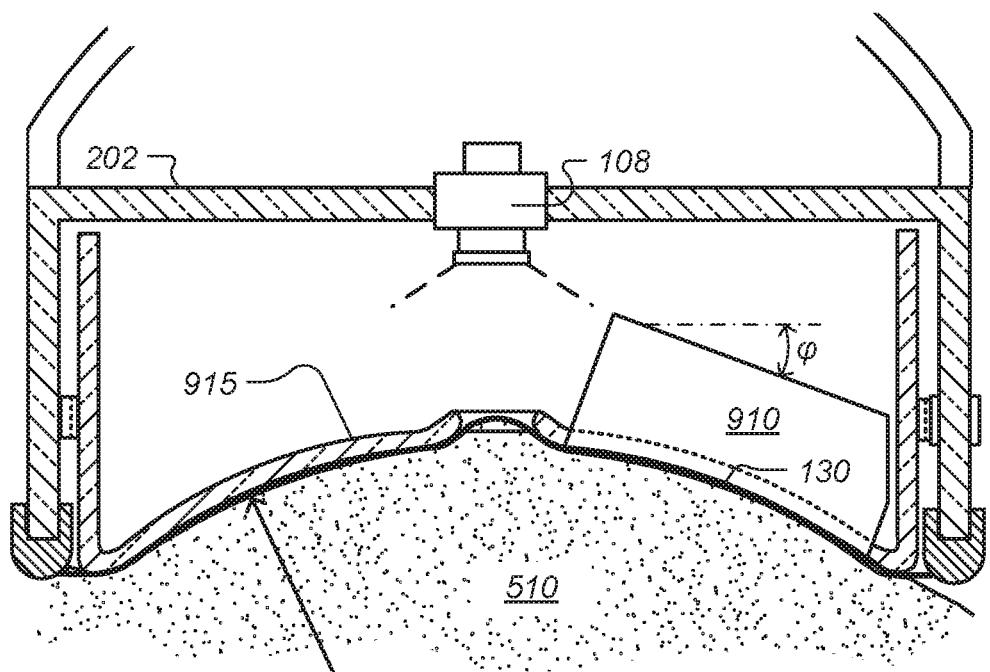
FIGS. 9A-9C illustrate a curved transducer mounted on a curved scanning template, according to some embodiments.
Figure 9B:
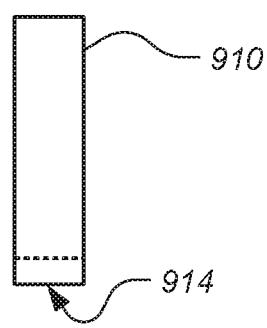
Figure 9C:
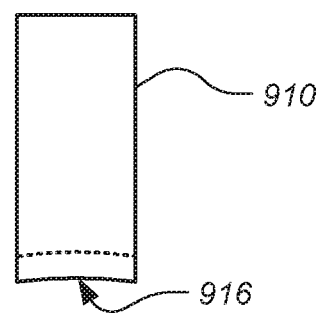

FIGS. 9A-9C illustrate a curved transducer mounted on a curved scanning template, according to some embodiments. Shown in FIG. 9A is curved transducer 910 mounted to a curved scanning template 915. The shape of the lower surface of template 915 can be approximately spherical. This configuration helps the fabric membrane better hold the breast with more comfort. According to some embodiments, the average angle φ preferably is kept to 15 degrees or less to reduce or minimize the breast thickness across the scan and thus allow for higher transducer frequency operations. This is particularly beneficial in cases of larger breasts. According to some embodiments, the curvature of templates 915 and 910 preferably has a radius of curvature r of more than 20 cm. According to some preferred embodiments, the radius of curvature r is more than 30 cm, or even more. FIGS. 9B and 9C shown that the lower surface of transducer 910 along its short dimension can be flat (surface 914 in FIG. 9B) or curved (surface 916 in FIG. 9C).

Figure 10A:
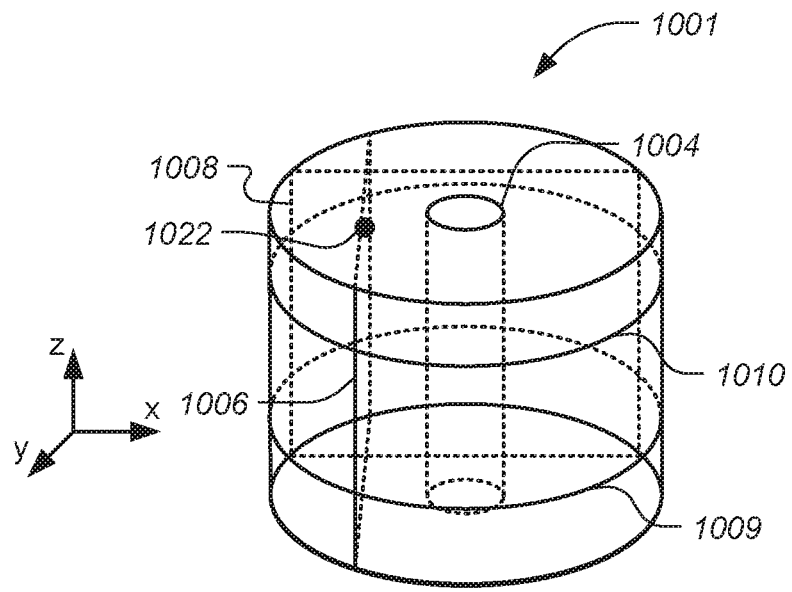
FIGS. 10A, 10B, 10C, and 10D illustrate further aspects relating to image processing, including CAD, and display of images by a breast ultrasound scanning system, according to some other embodiments.
Figure 10B:
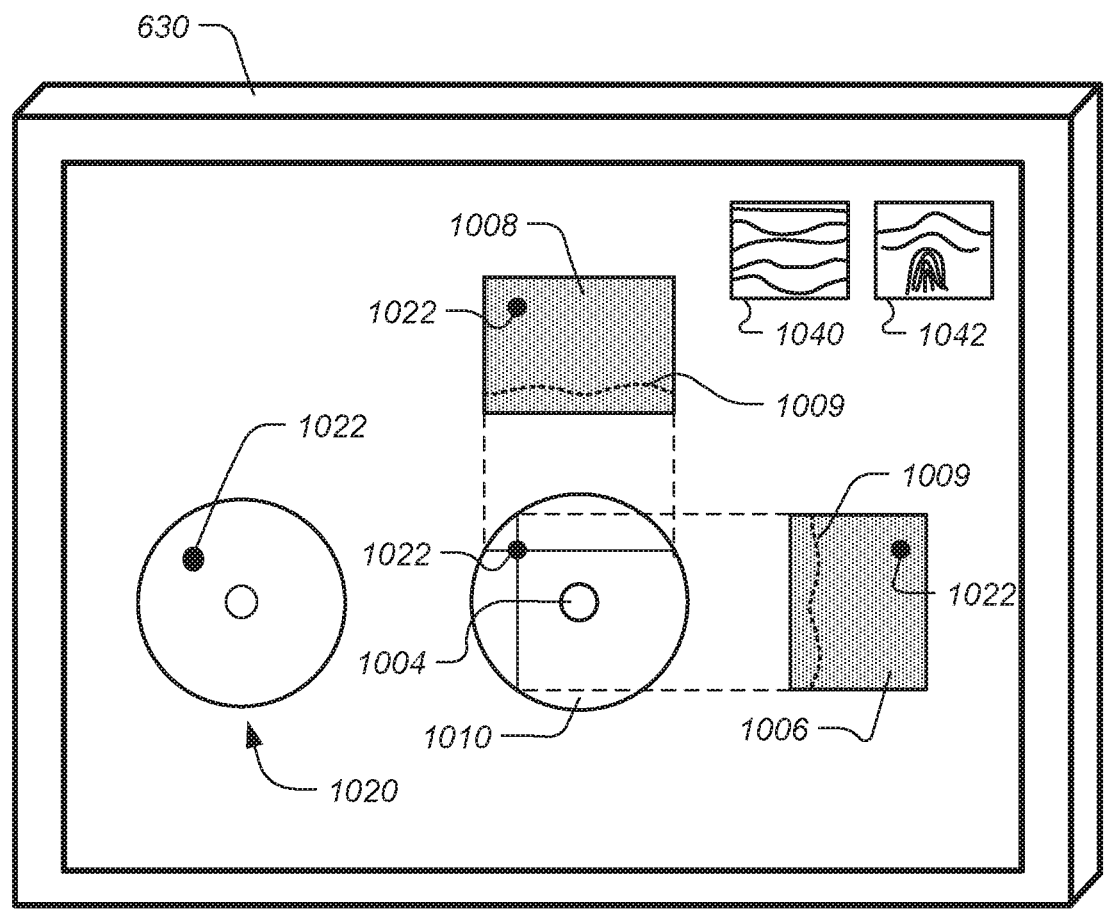

FIGS. 10A and 10B illustrate further aspects relating to image processing, including CAD, and display of images by a breast ultrasound scanning system, according to some embodiments. FIG. 10A illustrates a reconstructed 3D volume 1001 from approximate 1,000 2D scan slices of the breast. The center hole 1004 represents the nipple hole. A stack of coronal slices is constructed parallel to the chestwall plane 1009. These coronal slices can represent selected thicknesses of breast tissue, for example a slice that is 0.2 cm thick, or 0.5 cm, or 1 cm, or some other thickness, FIG. 10B shows a display which can be display 630 on cart 620 as shown in FIGS. 6 and 7A or can be another display used by a radiologist or other reviewer. A navigator image 1020 depicts the results of CAD, computed from the volumetric images shown in FIG. 10A. A suspicious lesion 1022 is shown in the navigator image 1020. By placing the mouse cursor over the suspicious lesion in the navigator image 1020 or otherwise pointing to the lesion, the system is configured to automatically show where the suspicious lesion 1022 appears in one or more of three 2D images: (a) a coronal image 1010, (b) the constructed 2D plane 1008, and (c) a reconstructed orthogonal 2D image 1006, which is orthogonal to slice 1008. Coronal images such as 1010 and slices images such as 1008 and 1006 can be derived by computer processing the 3D image of the breast using known techniques. These three 2D images and their relative special relationships are also shown in FIG. 10A. This method of using the CAD navigator image as a guide to the suspicious lesion in three 2D images can be very important to the reader physician in the determination of the degree of suspiciousness and in speeding up the assessment of a patient study. The CAD navigator image shows all the abnormalities found with CAD computation of the volumetric data. The navigator image 1020 can further show the degree of suspiciousness of the abnormalities found. With the help of CAD, the reader physician can go with confidence and speed through the information that the 1000 or so 2D images provide.

Also shown in FIG. 10B on the display screen, two small images are shown, representing respectively the hand-held scan results of the axilla area (image 1040) and the nipple area (image 1042).

Figure 10C:
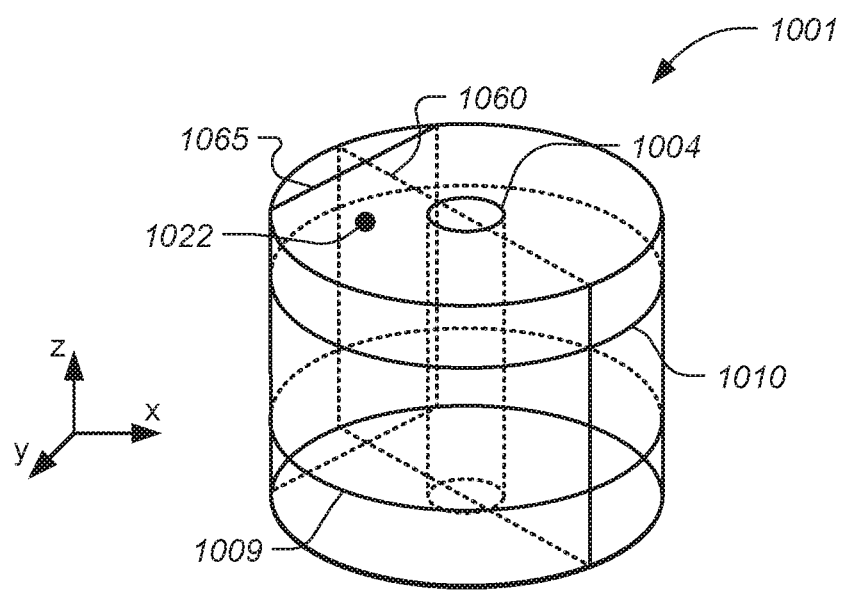
Figure 10D:
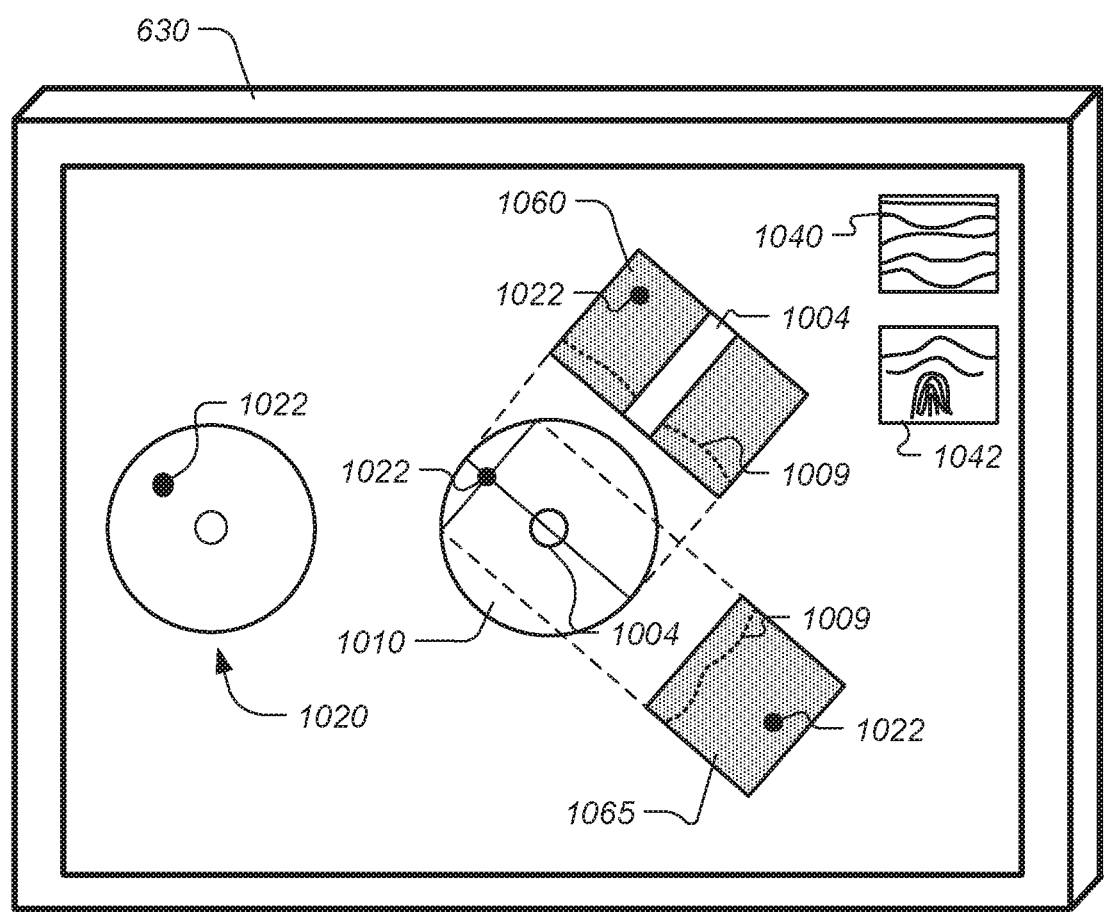

FIGS. 10C and 10D are otherwise similar to FIGS. 10A and 10B but show a slice image 1060 that is an original image of a radially oriented thin slice of the breast and image 1009 that represents a breast slice that is orthogonal to the slice in image 1060. In this example, navigator image 1020 shows a suspicious area 1022 and, in response to a user pointing to that area in the navigator image, for example with a cursor, the system automatically shows the original slice image 1060 that contains that suspicious area and an image 1065 of a slice that is orthogonal to the slice of image 1060 and contains the same suspicious area. In some cases, a display such as in FIG. 10D may be preferred over a display such as in FIG. 10B because the original slice image seen in FIG. 10D is an image of a type that may be more familiar to a physician reading the patient study. FIG. 10D also shows optional images 1040 and 1042 that come from hand scans. The system can be configured to show a variety of sets and sequences of images, for example, to show the 2D original images as they are being generated, radially oriented images conforming to any desired orientation through a 3D image of the breast, coronal images in a sequence or in a set, selected thicknesses of coronal images, or other sets of sequences of images.

Figure 11A:
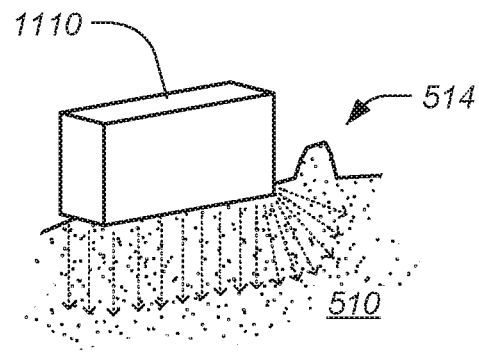
FIGS. 11A and 11B illustrate a transducer configured with a spreading beam to cover the nipple area for use with a breast ultrasound scanning system, according to some embodiments-.
Figure 11B:
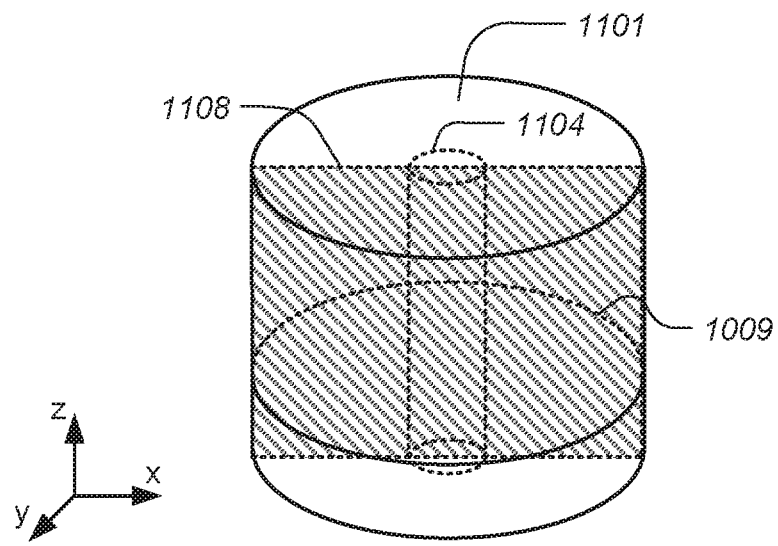

FIGS. 11A and 11B illustrate a transducer configured with a spreading ultrasound beam to cover the nipple area for use with a breast ultrasound scanning system, according to some embodiments. In this case scanning transducer 1110 is configured to spread the scanning beam under the nipple 514 to cover the nipple area of breast 510. Transducer 1110 can be used with a scanning system as described herein (e.g. instead of transducers 110 and/or 910). FIG. 11B shows that the resultant reconstructed 3D volume 1101 would not have a nipple hole 1104. For example, a constructed 2D plane image 1108 does not have a gap in the nipple region.

Although many of the embodiments of rotary scanning system are described herein as designed for breast cancer screening on asymptomatic patients, according to some embodiments, the described systems perform diagnostic exam on symptomatic patients. Some special diagnostic techniques, such as "elastography", "microbubble contrast imaging", and "contrast subtraction imaging" could be better performed with the rotary scanner disclosed herein. Simple elastography can be carried out by comparing images from two compressions of different pressures. The high probability lesions would show less volumetric distortion with increased pressure compression. Volumetric imaging is very suited to microbubble contrast imaging since the microbubbles disappear very quickly. Contrast subtraction imaging can be done by subtract volumetric images before and after contrast injection. Also, a suspicious lesion could be easily followed over time to observe its changes.

Whereas many alterations and modifications of the examples described above will no doubt become apparent to a person of ordinary skill in the art after having read the foregoing description, it is to be understood that the particular embodiments shown and described by way of illustration are in no way intended to be considered limiting. By way of example, it is to be appreciated that any of a variety of different frame assemblies can be used that position, compress, rotate, and otherwise manipulate the scanning template, whether the scanning template and/or any membrane used therewith are permanently used and re-used for different patients or one or both of them are disposed after each patient, without departing from the scope of the present teachings. Moreover, in one or more alternative preferred embodiments, the basic profile of the radial scanning template can be elliptically shaped, etc., rather than strictly circular-shaped as indicated in some of the attached drawings. The scanning surface of the ultrasound transducer can be arched or make to conform to another curved surface in a similar manner, if desired. The specification above refers to scanning the breast of a supine patient, but some deviation from a supine position is allowable, such as having the patient lying partly or even mostly on her side while her breast is being scanned with the transducer in the pod. Therefore, references to the details of the embodiments are not intended to limit their scope.

The invention claimed is:

1. An automated system for scanning a patient's breast with ultrasound, comprising:
a scanning pod having:
a housing, a scanning template secured to the housing and configured to rotate relative to the housing, said template having a nipple hole;
a viewing facility configured to provide a user with a view of the template;
said viewing facility comprising a camera and a camera display, wherein the camera is configured to view both the template and the breast compressed by the template to provide an operator with a live image on said camera display showing whether the breast compressed with said template is in wet contact with the template and what portion of the breast is in contact with the template;
wherein said template is essentially planar or has an opening angle greater than 150 degrees or a radius greater than 20 cm;
at least one transducer radially extending outwardly from the template's nipple hole and integrated with the template to rotate therewith; and
a motor configured to rotate the template and the at least one transducer relative to the housing;
wherein said scanning pod is configured to compress the patient's breast toward the patient's chest wall to thereby at least partly flatten the breast, with the breast's nipple aligned with the nipple hole of the template;
wherein said at least one transducer is configured to make ultrasound contact with the breast while the scanning pod is pressing the breast, and to rotatably scan the breast with said at least one transducer to thereby generate plural, radially oriented, original two-dimensional (2D) images of the breast;
a computer processing system configured to receive said 2D original images and to process them into at least one three-dimensional (3D) image of the breast; and
an ultrasound image display coupled with the processing system to display at least some of said images
a pressure sensor configured to measure and display an indication of pressure that the template or the transducer exerts on the breast; and
an acoustically transparent membrane between the patient's breast and the template and transducer.

2. The system of claim 1, in which said camera is supported in an interior space of said scanning pod.

3. The system of claim 2, further including a patient table with an opening into which a prone patient's breast extends, wherein the pod is configured to move up relative to the table to compress the patient's breast.

4. The system of claim 3, in which the template has an opening angle greater than 175 degrees and therefore is essentially flat.

5. The system of claim 2, in which said membrane is gel-impregnated.

6. The system of claim 5, wherein said membrane has a nipple hole through which the breast nipple protrudes into said nipple hole of the template.

7. The system of claim 1, wherein said viewing facility further comprises a viewing window in the housing.

8. The system of claim 1, in which the template has an opening angle greater than 175 degrees and therefore is essentially flat.

9. The system of claim 1, in which said at least one transducer remains laterally spaced from the breast nipple during said scan.

10. The system of claim 1, in which said at least one transducer is configured to emit an ultrasound beam that spreads laterally under the breast's nipple and provide image data for a volume under the nipple.

11. The system of claim 1, in which said acoustically transparent membrane is visually transparent and remains stationary relative to the breast and the housing during scanning.

* * * * *